United States Patent [19]

McClellan et al.

[11] Patent Number: 4,941,360
[45] Date of Patent: Jul. 17, 1990

[54] CONTINUOUS (FLEXIBLE) SEWAGE MONITORING MACHINE FOR SAMPLING BUILDING EFFLUENT TO MEASURE FOR CERTAIN CONTROLLED SUBSTANCES

[76] Inventors: Oliver B. McClellan, 1101 Post Oak Blvd. #300-318, Houston, Tex. 77056; Samuel J. Castorani, 4545 Post Oak Pl., #310, Houston, Tex. 77027

[21] Appl. No.: 366,646

[22] Filed: Jun. 14, 1989

[51] Int. Cl.$^5$ .............................................. G01N 1/14
[52] U.S. Cl. .............................. 73/864.34; 73/863.83
[58] Field of Search ........... 73/863.31, 863.32, 863.82, 73/863.83, 863.84, 864.21, 864.31–864.35, 864.73, 864.81

[56] References Cited

U.S. PATENT DOCUMENTS

| | | | |
|---|---|---|---|
| 2,675,706 | 4/1954 | Edgar | 73/863.33 |
| 3,555,910 | 1/1971 | Spence et al. | 73/863.83 |
| 3,719,081 | 3/1973 | Lynn et al. | 73/864.34 |
| 3,813,945 | 6/1974 | Crumal | 83/864.31 |
| 3,832,904 | 9/1974 | Dreuw et al. | 73/864.31 |
| 4,022,059 | 5/1977 | Schontzler et al. | 73/864.35 |
| 4,024,766 | 5/1977 | Perry | 73/864.35 |
| 4,415,011 | 11/1983 | Grant | 73/864.34 |

Primary Examiner—Robert Raevis

[57] ABSTRACT

Effluent sampling process for drug detection.

1 Claim, 2 Drawing Sheets

CONTINUOUS (FLEXIBLE) SEWAGE MONITORING MACHINE FOR SAMPLING BUILDING EFFLUENT TO MEASURE FOR CERTAIN CONTROLLED SUBSTANCES

FIELD OF THE INVENTION

Environmental engineering.
Wastewater monitoring.
Wastewater instrumentation.
Sewage sampling.
Drug testing.
Sampling building effluent.

BACKGROUND OF THE INVENTION

This invention was developed to measure on a continuous basis the effluent in sewage lines in order to obtain representative samples for the measurement in a fluorescence polarization immunoassay (FPIA) device for the presence of controlled substances in the effluent from a building or structure. Applicants have no information showing this process has been heretofore developed and utilized. This process is original.

In addition, certain patent claims are here filed in order to obtain samples on a continuous basis with flexible probes through a sample tap into the sewage pipeline. Heretofore, such devices sampled at fixed intervals, omitting some samples, and without probes into the effluent stream sufficiently flexible to ignore various non-predictive solids. With the pending application, more accurate samples can be taken with our device for analysis in standard drug detection devices.

The joint inventors have completed this application as a result of discussions over the past five years of means to improve upon current drug detection procedures and devices on a basis which is cost-effective, is non-intrusive to the person or persons to be tested, and is non-invasive of the legal rights of the person or persons to be tested.

Applicants also foresee the testing process to be an innovative and cost-effective means to develop support for a drug-free workplace or for any structure by developing affirmative peer pressure within the workforce or population in the structure to avoid drugs of abuse.

SUMMARY OF THE INVENTION

The (1) invention consists of (2) a (flexible) probe with three entry points to obtain samples of effluent from sewage pipe by means of a sample tap. The probe then attaches to (3) an aspirator which operates on variable levels of effluent on a continuous basis to extract the samples needed to monitor the effluent. The samples thus obtained will be in a sufficient level of dilution (down to one nanogram) to permit testing for controlled substances on existing FPIA devices on a continuous basis over a timed interval of up to twelve hours. (4) All samples will be handled with intruments and sample cups, the latter being covered with a protective coating in order to eliminate any cross-contamination.

BRIEF DESCRIPTION OF THE DRAWINGS

FIG. one is a side view of the schematic for the entire machine process.
FIG. two is a detail of the probe and its use in a standard controlled sewage tap line.

DETAILED DESCRIPTION OF THE INVENTION

Figure 1:
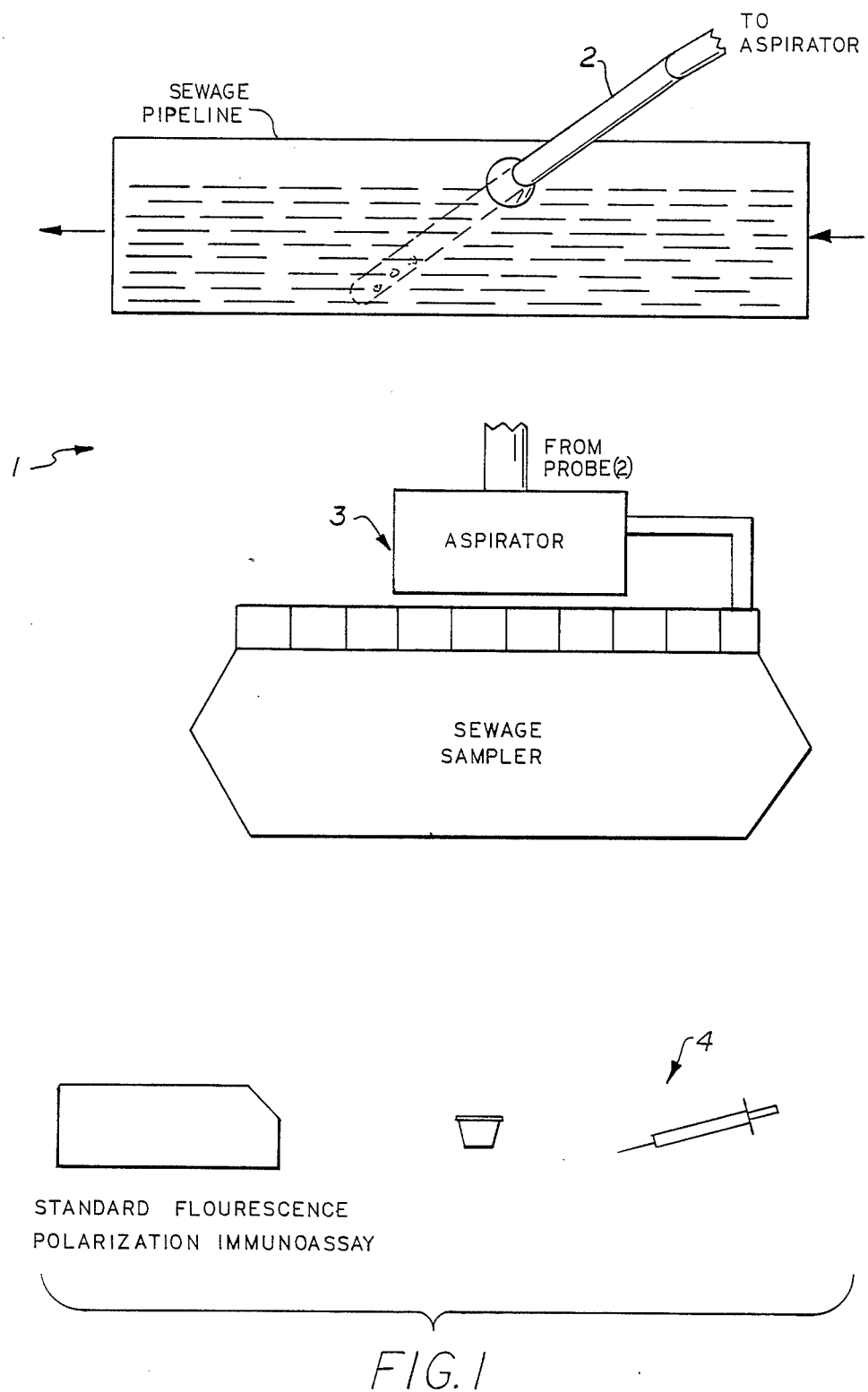
Figure 2:
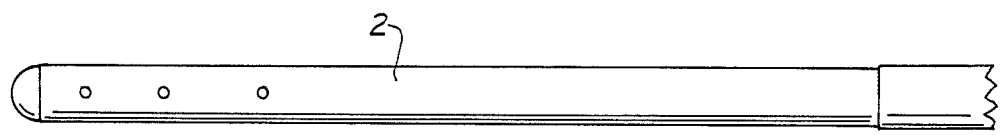
Figure 2:
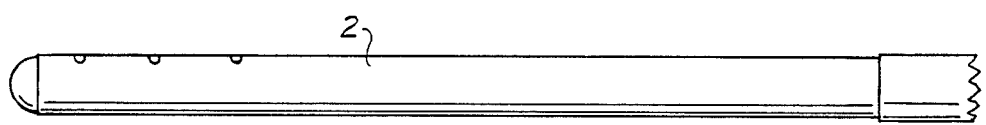
Figure 2:
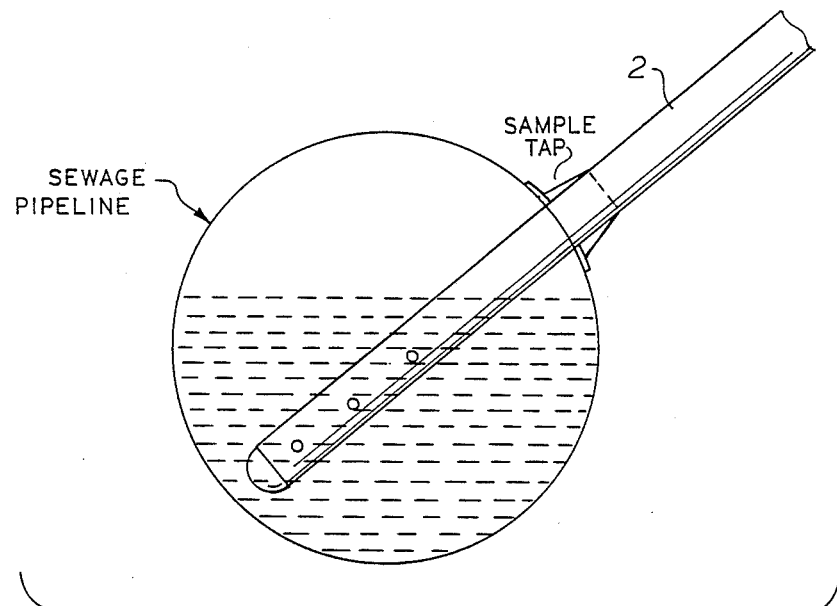

Pursuant to 35 U.S.C. Sec. 112, the following description of the invention and of the manner and process of making and using it is submitted:

The probe is a plastic tube with three holes on one side. The extended end of the probe is closed. The probe is placed in the effluent pipeline stream through a sample tap which is non-prejudicial to the wastewater flow. The opposite end of the probe is attached to an aspirator which draws the sample on a controlled basis which is continuous while permitting various sample holders to be rotated on a standard sewage sampler. The aspirator can be adjusted for volumes of sample to be extracted and is self-adjusting for the levels of effluent being measured.

The sample thus obtained are subject to analysis in standard high-sensitivity drug analysis devices capable of determining the presence of cannaboids, amphetamines, methamphetamines, cocaines, ethanol, phencyclines, barbiturates, and opiates.

The purpose is to obtain samples from the sewage effluent system of a structure or building in order to analysis the urine from the occupants for determination of the presence of controlled substances, and other substances emitted in urine or feces, for purposes of analysis. The benefit and utility is to have a machine capable of undertaking a first-line analysis for abuse of controlled substances on a cost-effective basis while avoiding any invasion of privacy or instrusion into a person's body or its functions.

What is claimed is:

1. A sampling system to obtain samples from the sewage effluent system of a structure or building for the purpose of collectively analyzing the urine and/or feces from the occupants of the structure or building for determination of the presence of controlled substances in a non-intrusive manner, said sampling system comprising a hollow, flexible, elongated probe extending in a non-horizontal direction through a sample tap of a effluent pipeline associated with the structure or building, the probe including a plurality of openings positioned along its elongated wall portion, and collectively in a direction parallel to the longitudinal axis of the probe, to permit sample to flow into the probe, and a closed first end; a fluidic line having two ends, the first end of the fluidic line being coupled to a second open end of the elongated probe that is positioned outside of the pipeline; an aspirator fluidly coupled to the second end of the fluidic line to draw sample from the pipeline through the plurality of openings, probe and fluidic line, and subsequently deposit the sample into a sample holder, the sample holder being only one of a plurality of sample holders that are sequentially filled in an automatic manner with an equal number of samples over a predetermined period of time, whereby the samples in the holders are subsequently analyzed for controlled substances, whereby the occupants of the structure or building are collectively tested for use of controlled substances in a nonintrusive manner.

* * * * *